(12) United States Patent
Glynn

(10) Patent No.: US 7,853,315 B2
(45) Date of Patent: Dec. 14, 2010

(54) NON-INVASIVE SPECTROPHOTOMETER

(75) Inventor: Christopher Glynn, Gaunt Mill, Rack End, Standlake, Oxon (GB) OX29 7OA

(73) Assignee: Christopher Glynn, Oxford (GB)

( * ) Notice: Subject to any disclaimer, the term of this patent is extended or adjusted under 35 U.S.C. 154(b) by 876 days.

(21) Appl. No.: 10/468,279

(22) PCT Filed: Mar. 8, 2002

(86) PCT No.: PCT/GB02/01083

§ 371 (c)(1),
(2), (4) Date: Aug. 19, 2003

(87) PCT Pub. No.: WO02/071932

PCT Pub. Date: Sep. 19, 2002

(65) Prior Publication Data

US 2004/0133093 A1 Jul. 8, 2004

(30) Foreign Application Priority Data

Mar. 9, 2001 (GB) ................................ 0105784.3

(51) Int. Cl.
*A61B 6/00* (2006.01)
(52) U.S. Cl. ....................... 600/476; 600/477; 600/480; 351/204; 351/205; 351/206
(58) Field of Classification Search ......... 600/309–344, 600/407, 408, 473–480; 351/204, 205, 206, 351/210, 221
See application file for complete search history.

(56) References Cited

U.S. PATENT DOCUMENTS 4,157,708 A 6/1979 Imura (Continued)

FOREIGN PATENT DOCUMENTS

EP 0 122 961 A 10/1984

(Continued)

OTHER PUBLICATIONS

Laing et al; "The Choroidal Eye Oximeter: An Instrument for Measuring Oxygen Saturation of Choroidal Blood in Vivo"; IEEE Transactions on Biomedical Engineering, May 1975, USA, vol. BME-22, No. 3, pp. 183-195, XP002200046.

*Primary Examiner*—Long V Le
*Assistant Examiner*—SanJay Cattungal
(74) *Attorney, Agent, or Firm*—Nixon & Vanderhye P.C.

(57) ABSTRACT

A device for use in non-invasive monitoring of a human or animal subject's bodily functions in vivo, comprises:
  a first optical system for identifying the center (1) of a pupil (13) of an eye of the subject, said first system comprising a first light source (2) for directing light towards the eye, first receiving means for receiving light reflected from the iris (4) of the eye, and first processing means for determining the position of the center (1) of the pupil (13) from the light reflected (3) from the iris;
  a second optical system comprising a second light source (14) directing light to a focussing means (15) for focussing light in the plane of the pupil (13) and for directing the focussed light onto the retina (10) of the eye, a second receiving means for receiving light reflected (17) from the retina and back through the pupil (13), and second processing means for analyzing the light reflected from the retina (10); and
  alignment means for aligning the second system with the center (1) of the pupil (13) as determined by the first system.

14 Claims, 3 Drawing Sheets

U.S. PATENT DOCUMENTS

| | | | |
|---|---|---|---|
| 4,402,325 A | | 9/1983 | Sawa |
| 4,533,221 A | * | 8/1985 | Trachtman .................. 351/203 |
| 4,660,945 A | * | 4/1987 | Trachtman .................. 351/203 |
| 5,002,384 A | * | 3/1991 | Trachtman .................. 351/203 |
| 5,016,643 A | * | 5/1991 | Applegate et al. ........... 600/558 |
| 5,210,554 A | * | 5/1993 | Cornsweet et al. .......... 351/206 |
| 5,231,430 A | * | 7/1993 | Kohayakawa ............... 351/243 |
| 5,297,554 A | * | 3/1994 | Glynn et al. ................. 600/476 |
| 5,360,010 A | * | 11/1994 | Applegate et al. ........... 600/558 |
| 5,553,617 A | | 9/1996 | Barkenhagen |
| 5,632,282 A | * | 5/1997 | Hay et al. ................... 600/558 |
| 5,784,145 A | | 7/1998 | Ghodse et al. |
| 5,919,132 A | | 7/1999 | Faubert et al. |
| 6,231,188 B1 | * | 5/2001 | Gao et al. .................... 351/227 |
| 6,494,576 B1 | * | 12/2002 | L'Esperance, Jr. .......... 351/206 |
| 6,574,432 B2 | * | 6/2003 | Nanjyo ........................ 396/18 |
| 6,853,854 B1 | * | 2/2005 | Proniewicz et al. ......... 600/319 |
| 2002/0091321 A1 | * | 7/2002 | Goldstein et al. ........... 600/476 |
| 2002/0151774 A1 | * | 10/2002 | Soller et al. ................. 600/318 |
| 2006/0200013 A1 | * | 9/2006 | Smith et al. ................. 600/319 |

FOREIGN PATENT DOCUMENTS

| | | |
|---|---|---|
| EP | 0 589 191 A | 3/1994 |
| GB | 2 248 297 | 4/1992 |
| WO | 95/24152 A | 9/1995 |
| WO | WO 98/43533 | 10/1998 |

* cited by examiner

NON-INVASIVE SPECTROPHOTOMETER

This application is the U.S. national phase of international application PCT/GB02/01083 filed 8 Mar. 2002, which designated the U.S.

FIELD OF THE INVENTION

The present invention relates to a device for use in non-invasive monitoring of a human or animal subject's bodily functions in vivo. The device relates, more particularly, to such monitoring that uses light beams directed at, and reflected from, various parts of the subject's eye(s) to provide analysable data.

Monitoring the functions of a human or animal body is necessary in many different situations. In the past, blood sample gave been taken from the patient or animal and constituents have been measured by spectrophotometry. It is also known to relatively invasively measure the constituents in the blood of the patient or of the animal by bringing the spectrophotometer into contact with the patient or the animal, by for example using modified contact lens systems. The eye, which is the only part of the body that is designed to transmit light, thus acts as the curvette for the spectrophotometer.

BACKGROUND ART

The use of spectrophotometric techniques for monitoring the level and variation of one or more parameters indicative of body condition is well known. Thus, U.S. Pat. Nos. 4,157,708 and 4,402,325 disclose ophthalmic devices incorporating one or more plethysmograph assemblies, but these devices have the disadvantage that light is assumed to be introduced along the axis of the pupil of the subject's eye.

In addition, U.S. Pat. Nos. 5,553,617 and 5,919,132 describe further non-invasive methods of measuring body conditions but, again, light introduced into the eye is assumed to be directed along the axis of the pupil.

SUMMARY OF THE INVENTION

It is therefore a first aim of the present invention to overcome the disadvantages of the prior art by providing a non-invasive spectrophomeric system, which ensures that light, used to monitor the body condition of a subject, is directed along the axis of the eye by being focused in the centre of the plane of the iris, which is otherwise known as being the Maxwellian view of the pupil.

It is a second aim of the present invention to provide such a system that minimises the potential injury to the iris and other structures of the eye, should light (used for spectrophotometric analysis) not be directed through the pupil in Maxwellian view, thus overcoming another disadvantage of the prior art.

A third aim of the present invention is to allow measurement of the amount of light illuminating the eye by focusing the light in Maxwellian view.

Thus, in a first aspect, the present invention provides a device for use in non-invasive monitoring of a human or animal subject's bodily functions in vivo, comprising:

(a) a first optical system for identifying the centre of a pupil of an eye of the subject, said first system comprising a first light source for directing light towards the eye, first receiving means for receiving light reflected from the iris of the eye, and first processing means for determining the position of the centre of the pupil from the light reflected from the iris;

(b) a second optical system comprising a second light source directing light to a focusing means for focusing light in the plane of the pupil and for directing the focused light onto the structures within the eye, a second receiving means for receiving light structures from the structure and back through the pupil, and second processing means for analysing the light reflected from the structure; and (c) alignment means for aligning the second system with the centre of the pupil as determined by the first system.

The device therefore comprises at least three major components.

The first major component the first optical system, is preferably provided by modifying a standard pupillometer, such as that described in U.S. Pat. No. 5,784,145. Further, the general principles of using pupillometry in this context are described in the applicant's previous International Patent Application No. WO/90/12534.

The second major component, that is the second optical system, is usually provided by modifying a standard spectrophotometer and the general principles of using such spectrophotometric techniques are again described in the applicant's prior International Patent Application No. WO/90/12534. A typical example of the type of structure within the eye onto which light is focused is the retina. In the spectroscopy field, the eye is in effect the curvette of the body, since it is the only part of the body that is designed to transmit light. Thus, measurement of the characteristics of light reflected from the eye can give an indication of characteristics of bodily functions in general.

Typically, the third major component, that is the alignment means, is controllable either directly by, or independently of, the subject, for example by use of manually operated lever(s), button(s), joystick(s) and/or one or more computer mice. The alignment means provides' a variable focus capability to the system and may optionally operate in an automatic way without personal intervention from either the subject or the clinician. Indeed, activation of such alignment may also be automatically initiated by the first optical system, once the centre of the pupil in Maxwellian view has been determined.

In one embodiment, the device is arranged to project an image processed by the first processing means onto the retina of the operator (whether the subject or not), so as to allow the operator to be able to perceive when the position of the centre of the pupil has been determined and so be able to operate the alignment means appropriately.

In addition, the device may be arranged to gather data from either a selected eye or from both eyes of the subject, that is, to be a monocular or binocular system.

Typically, the first light source emits infra-red light, for example from one or more LED(s).

Preferably, the second receiving means comprises one or more crystal charged device (ccd)-type camera(s).

In one embodiment, the first optical system is adapted to monitor, in particular, the location of the edge(s) of the pupil(s), so as to allow calculation of the centre of the pupil(s) by the first processing means.

Preferably, the first and second light sources comprise one or more optical fibre(s) for transmitting light towards the eye(s). In a particularly preferred arrangement, the optical fibre(s) are arranged to function as both the light input means and the light receiving means.

In one embodiment the second light source and the second receivina means are arranged to monitor the intensity of light of a selected wavelength returning from the retina(s) of the eye(s).

In an alternative embodiment, the second light source and second receiving means are arranged to monitor the intensity of light of different wavelengths returning from the retina(s) of the eye(s), thereby enabling an absorbance/reflectance characteristic of the retina(s) to be determined.

The first and second optical systems may have parts in common. Thus, for example, the first and second receiving means can optionally be provided by the same unit. Likewise, the first and second processing means can also be the same processing means, if desired.

The expression "human and bodily functions" used herein is intended to include the wide variety of different functions that a medical or veterinary practitioner may wish to non-invasively monitor or measure. In particular, it is intended to include the monitoring of any substances and changes in the blood of the retina and any biochemical (organic or inorganic) changes in the cells of the retina of the subject. In addition, any or all of these changes can be monitored in conjunction with changes in the electrical, biochemical or pathological activity of the retina or of the brain.

The term "light" used herein is, unless otherwise specified, intended to include visible wavelengths and non-visible wavelengths such as infra-red and ultra-violet light, that are non-injurious to the eye and the structures contained within the eye.

The present invention will now be described in further detail by way of the following non-limiting examples with reference to the drawings, in which:

BEST MODE

Figure 1:
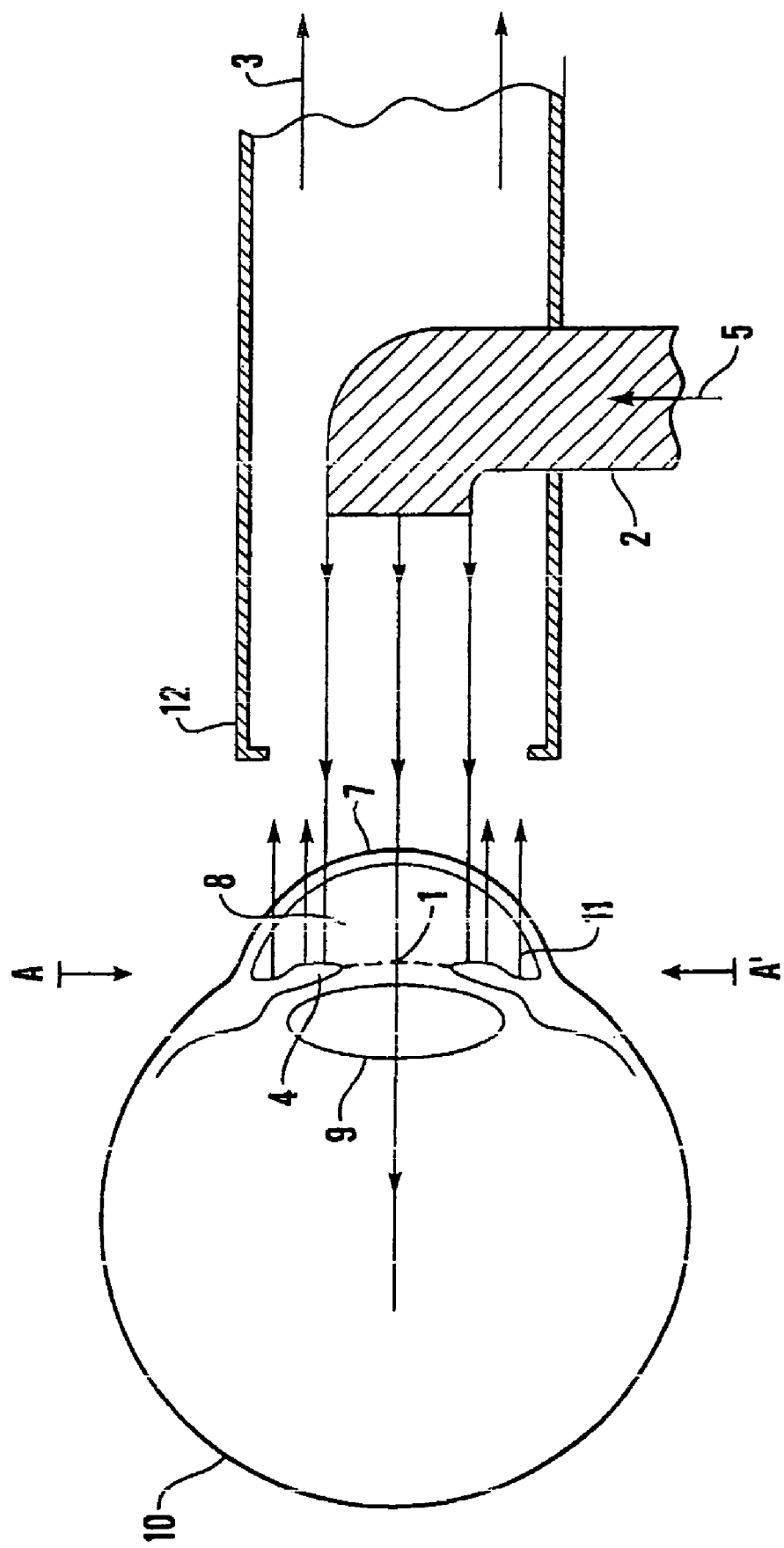
FIG. 1 shows a schematic representation of the first optical system of an embodiment of the present invention.

In FIG. 1, a first optical system is shown that is capable of identifying the centre 1 of a pupil of an eye of a subject. This first system comprises a first light source 2 that directs light of an infra-red wavelength towards the eye, a first receiving means (not shown) that receives fight subsequently reflected 3 from the iris 4 of the eye, and a first processing means (not shown) that then determines the position of the centre 1 of the pupil from the light 3 so reflected from the iris 4.

Input light 5 is directed by one or a bundle of optical fibre(s) that constitute the first light source 2 and is emitted towards the eye. The device is enclosed in a housing 12 and, depending upon alignment of this housing 12, the focused light either passes through the pupil or alternatively is reflected by the iris 4. The latter light 11 is directed back into the housing 12 of the device and passes as a beam 3 of reflected light that can be detected by the first receiving means. Also shown in FIG. 1 are the anterior chamber 8 of the eye and the lens 9 of the eye.

Figure 2:
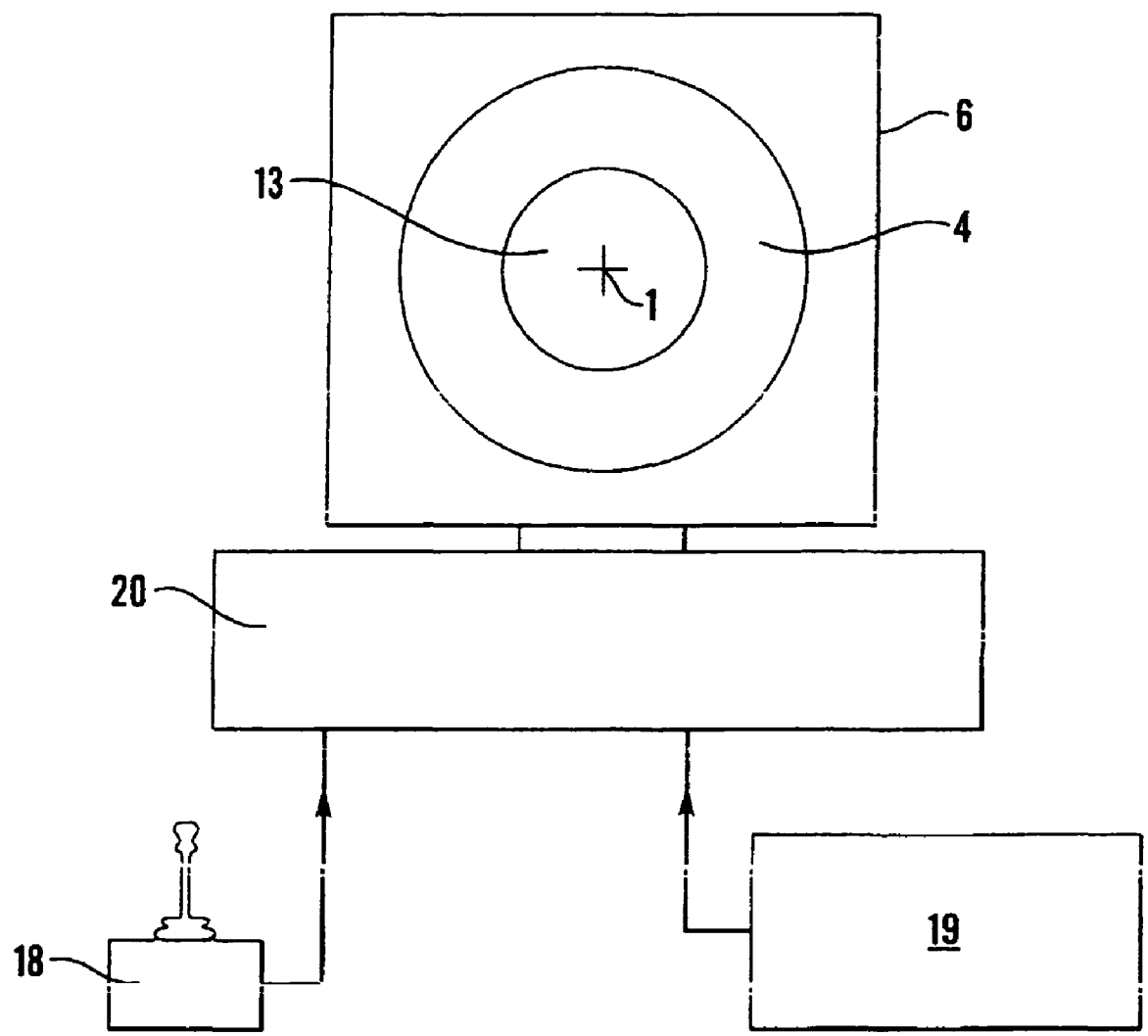
FIG. 2 illustrates an image of the eye on a computer screen, as may be used in one embodiment of the present invention.
Figure 3:
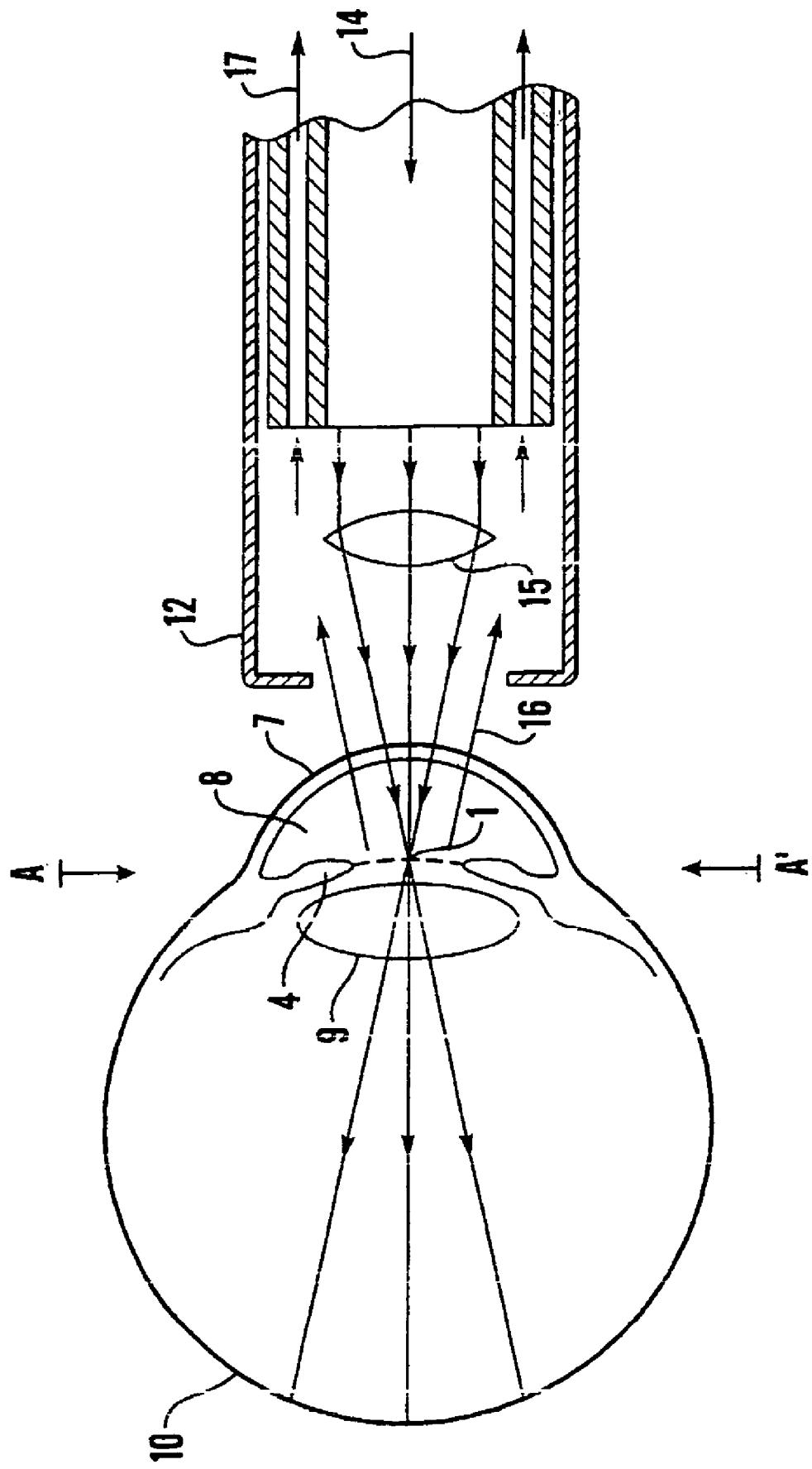
FIG. 3 shows a schematic representation of the second optical system of an embodiment of the present invention.

In FIG. 2, a Maxwellian view of the eye is shown on a computer screen 6, the view being a cross-sectional view of the eye about line A-A' in FIGS. 1 and 3. The, iris 4 is illustrated surrounding the centre 1 of the pupil 13. A computer-processing unit 20 represents the first and second processing means and the first and second optical systems are depicted as unit 19.

The first optical system is sequentially alignable with respect to the eye such that the first light source 2 directs infra red light either through the pupil 13 or onto the iris 4. Reflected light 11 from the iris forms a beam 3 that is analysed by the first processing means, so that the centre 1 of the pupil 13 can be determined. Typically, the pixels of the image produced by the beam 3 are analysed to determine the location of the circumference of the circle represented by the edge of the iris 4. In one option, the radius of the circle is then calculated by the first processing means, so that the location of the centre 1 can be identified, however other methods of similar calculation are clearly possible.

In FIG. 3, a second optical system is shown that comprises a second light source 14 directing light to a focusing means 15 for focusing light in the plane of the pupil 13 and for directing the focused light onto the retina 10 of the eye. A second receiving means (not shown) receives light 17 reflected from the retina 10 and back 16 through the pupil 13. A second receiving and processing means (not shown) is provided for analysing the light 17 that is reflected from the retina 10 and back through the pupil 13 into the housing 12 of the device.

Once the first optical system has been used to locate the centre 1 of the pupil 13, the alignment means (not shown) of the device can be used to align the second optical light so that light is shone through the centre 1 of the pupil 13 in the plane of the pupil 13, that is in a Maxwellian view. The alignment process can be effected by way of, for example, a joystick (18) (see FIG. 2), which can be operated by the physician, or the subject themselves. In this way, the operator can view an image of the eye being investigated on a screen 6 and, in conjunction, use the joystick 18 to align the second optical system with the centre 1 of the pupil 13.

However, the device may be arranged for example such that the first optical system operates automatically (i.e. without manual operation). Thus, the first optical system may directly activate the alignment means to position the second optical system into the correct alignment with the centre of the pupil, so as to provide a Maxwelllan view of the eye.

Further, instead of the operator viewing the image of the eye on a screen, such an image may be transferred directly onto the retina of the operator, for example by way of the second optical system itself.

As shown in FIG. 3, input light 14 is directed via an optical fibre from which it is emitted so as to pass through a focusing means 15 and out of the housing 12 of the device towards the centre 1 of the pupil 13. Light 16, which is reflected back from the retina 10 and back through the pupil 13, subsequently passes back into the device and travels as a beam 17 along one or more optical fibres to the second processing means.

The second processing means analyses the beam 17 to determine the absorbance/reflectance spectrum of the retinal blood supply. Any combination of mono-chromatic lights or white light, as well as wavelengths in the infra-red or ultra-violet spectra can be used. Specific, selected wavelengths permit optimal discrimination of the various blood components, as well as optimal discrimination of the various retinal biochemical functions and components.

In this way, it is, for example, possible to provide an accurate measurement of the oxygen saturation of the retinal blood flow and, since this is more proximal to blood flow in the toe, finger or ear (as measured by well known prior techniques), it can provide the clinician with a more accurate assessment of the oxygen content of blood delivered to the brain.

The system described above can be used for a wide range of applications. For example, it is possible to measure any, or all, of the constituents of the blood of a subject, in vivo. Additionally, when appropriate wavelengths are used, it is also possible to measure the constituents of the cells of the retina or to measure physiological and or pathological changes in the cells of the retina. It is possible to measure the biochemical activity of these cells, in real time.

Further, it is possible also to use the system to measure the unique DNA profile of any individual and thus provide security checks. For example, a monocular system can be used as part of a cash-dispensing machine, in which the identity of the person wishing to withdraw cash is checked via non-invasive DNA analysis of the retinal cells.

Whereas police currently use breathalysers to check a driver's blood alcohol levels at the road side, using the present system would not only allow such analysis to be more accurately performed, but would also allow analysis of any number of other drugs that can be detrimental to driving, which may also be present in a driver's blood.

Moreover, the system is also more suitable for monitoring the blood glucose levels of diabetic patients than conventional needle-based methods, since it is non-invasive.

It is also possible to measure changes in the arteries and veins of the retina, which may be an indication of generalised arterial and venous disease. Thus, in diabetic patients, who typically can suffer from such generalised arterial disease, it would be possible to non-invasively chart the progression of the disease.

Hence, in general, the system in effect provides the subject with the resources of a non-invasive, real time biochemical and haematological laboratory.

The system can measure visual evoked potentials more accurately than conventional means, because it is possible to give an accurate amount of light and so the amplitude of response can also be assessed. Conventionally, by contrast, only latency of response is measured. Thus, the present system allows for the assessment of any electrical activity of the retina, so that the activity of the visual areas of the brain can be assessed.

The measurements made possible with the present system can be of static samples or of continuous samples in real time.

Thus, the present invention provides a simple, yet effective way of ensuring that spectrophotometric analysis of a subject can be effected by aligning the light used so that it passes through the centre of the pupil(s) of the subject's eye(s) to provide a Maxwellian view. This ensures that the spectrophotometric measurements made can be accurate and that potential injury, that could otherwise ensue, to the subject's iris(es) and other eye structures is avoided.

The invention claimed is:

1. A device for use in non-invasive monitoring of a human or animal subject's bodily functions in vivo, comprising:
    a first optical system for identifying the centre of a pupil of an eye of the subject, said first system comprising:
        a first light source for directing light towards the eye,
        first receiving means for receiving light reflected from the iris of the eye, and
        first processing means for determining the position of the centre of the pupil from the light reflected from the iris;
    a second optical system comprising:
        a second light source for directing light to a focussing means for focussing light substantially in the centre of the plane of the pupil and directing the focussed light onto the retina of the eye and providing a Maxwellian view of the eye,
        second receiving means for receiving light reflected from the retina and back through the pupil and for monitoring intensity of at least one selected wavelength of said reflected light, and
        second processor means for analysing the light reflected from the structures and determining an absorbance/reflectance characteristic of said retina; and
    alignment means for aligning the second system with the centre of the pupil as determined by the first optical system.

2. A means as claimed in claim 1, wherein the alignment device is controllable either directly by, or independently of, the subject.

3. A means as claimed in claim 1, wherein the alignment device is controllable by use of manually operated lever(s), button(s), joystick(s) and/or one or more computer mice.

4. A device as claimed in claim 1, wherein the first and second receiving means are comprised by a single receiver.

5. A device as claimed in claim 1, wherein the first and second processing means are comprised by a single processor.

6. A device as claimed in claim 1, wherein the device is arranged to project an image processed by the first processing means onto the retina of said subject, so as to allow the operator to be able to perceive when the position of the centre of the pupil has been determined and so be able to operate the alignment means appropriately.

7. A device as claimed in claim 1, wherein the device is arranged to gather data from either a selected eye or from both eyes of the subject.

8. A device as claimed in claim 1, wherein the first light source comprises one or more light emitting diodes.

9. A device as claimed in claim 1, wherein the first or second receiving means is comprised of one or more charge coupled diode cameras.

10. A device as claimed in claim 1, wherein the first optical system is adapted to monitor the location of the edge(s) of the pupil(s) so as to allow calculation of the centre of the pupil(s) by the first processing means.

11. A device as claimed in claim 1, wherein the first and second light sources comprise one or more optical fibre(s) for transmitting light towards the eye(s).

12. A device as claimed in claim 11, wherein the optical fibre(s) are arranged to function both as a light source and a light receiver.

13. A device as claimed in claim 1, wherein the second light source and second receiving means are arranged to monitor the intensity of light of a selected wavelength returning from the retina(s) of the eye(s).

14. A device as claimed in claim 1, wherein the second light source and second receiving means are arranged to monitor the intensity of light of different wavelengths returning from the retina(s) of the eye(s), thereby enabling an absorbance/reflectance characteristic of the retina(s) to be determined.

* * * * *